United States Patent [19]

Hillstead

[11] Patent Number: 4,856,516
[45] Date of Patent: Aug. 15, 1989

[54] ENDOVASCULAR STENT APPARATUS AND METHOD

[75] Inventor: Richard A. Hillstead, Hollywood, Fla.

[73] Assignee: Cordis Corporation, Miami, Fla.

[21] Appl. No.: 295,129

[22] Filed: Jan. 9, 1989

[51] Int. Cl.⁴ .......................... A61M 29/00; A61F 2/06
[52] U.S. Cl. ........................................ 128/343; 604/96; 604/104; 623/1; 623/12
[58] Field of Search ...................... 623/1, 12; 128/343, 128/344, 334 R; 604/8, 96, 104

[56] References Cited

U.S. PATENT DOCUMENTS

| | | | |
|---|---|---|---|
| 3,490,975 | 1/1970 | Lightwood et al. | 623/1 |
| 4,140,126 | 2/1979 | Choudhury | 623/1 X |
| 4,503,569 | 3/1985 | Dotter | 623/1 |
| 4,733,665 | 3/1988 | Palmaz | 623/1 X |
| 4,739,762 | 4/1988 | Palmaz | 128/343 |

FOREIGN PATENT DOCUMENTS

| | | | |
|---|---|---|---|
| 0282175 | 9/1988 | European Pat. Off. | 623/1 |
| 1205743 | 9/1970 | United Kingdom | 623/1 |

*Primary Examiner*—Ronald L. Frinks
*Attorney, Agent, or Firm*—Watts, Hoffman, Fisher & Heinke Co.

[57] ABSTRACT

A stent for reinforcing a vessel wall is constructed from a single elongated wire. The wire is first bent into a series of tight bends. The wire is then further bent into a sequence of loops that are connected by half hitch junctions and interconnections which are either aligned or spiral around a circumference of the stent. The completed stent forms a cylindrical form which can be expanded from a initial diameter to a larger implanted diameter by application of a radially outward force from a balloon catheter or the like.

10 Claims, 2 Drawing Sheets

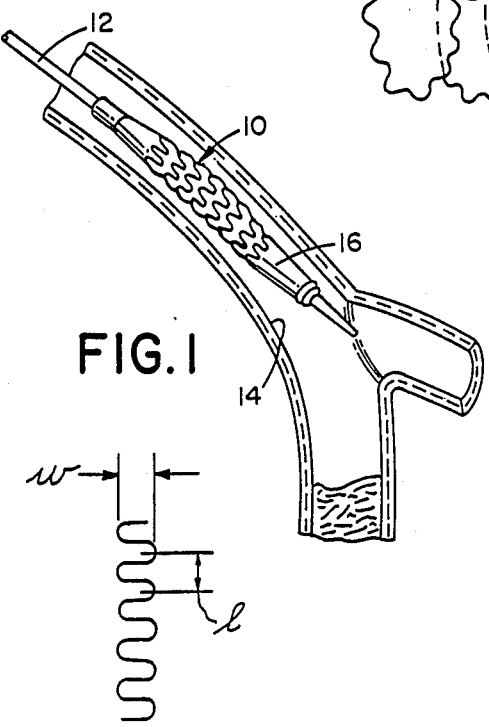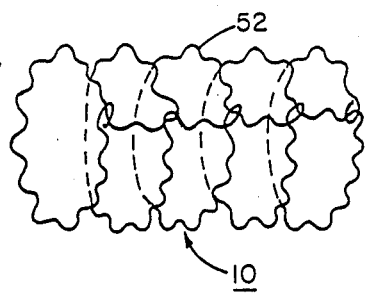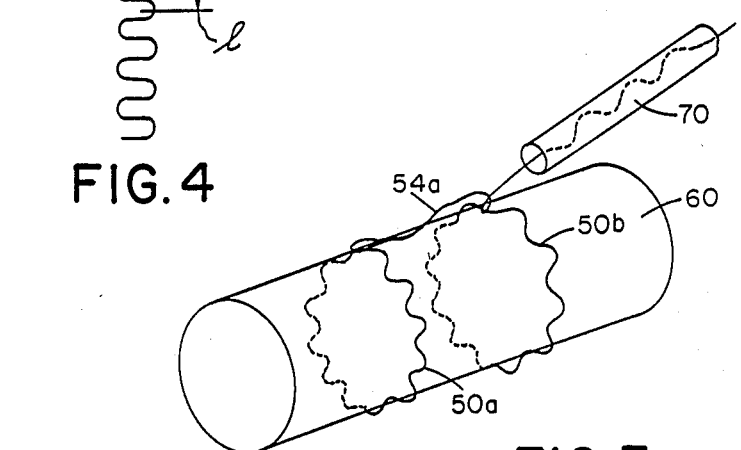

ENDOVASCULAR STENT APPARATUS AND METHOD

TECHNICAL FIELD

The present invention relates to an endoprosthesis device for implantation within a body vessel, typically a blood vessel.

BACKGROUND ART

A type of endoprosthesis device, commonly referred to as a stent, is placed or implanted within a blood vessel for treating stenoses, strictures, or aneurysms in the blood vessel. These devices are implanted within the vascular system to reinforce collapsing, partially occluded, weakened, or abnormally dilated sections of the blood vessel. Stents also have been successfully implanted in the urinary tract or the bileducts to reinforce those body vessels.

One common procedure for implanting the endoprosthesis or stent is to first open the region of the vessel with a balloon catheter and then place the stent in a position that bridges the weakened portion of the vessel.

Prior art patents refer to the construction and design of both the stent as well as the apparatus for positioning the stent within the vessel. One representative patent is U.S. Pat. No. 4,140,126 to Chaudhury which issued Feb. 20, 1979. This patent discloses a technique for positioning an elongated cylindrical stent at a region of an aneurysm to avoid catastrophic failure of the blood vessel wall. The '126 patent discloses a cylinder that expands to its implanted configuration after insertion with the aid of a catheter A second prior art patent to Dotter, U.S. Pat. No. 4,503,569 which issued Mar. 12, 1985 discloses a spring stent which expands to an implanted configuration with a change in temperature. The spring stent is implanted in a coiled orientation and heated to cause the spring to expand.

U.S. Pat. No. 4,733,665 to Palmaz which issued Mar. 29, 1988 discloses a number of stent configurations for implantation with the aid of a catheter. The catheter includes a mechanism for mounting and retaining the vascular prosthesis or stent, preferably on an inflatable portion of the catheter. The stent is implanted by positioning it within the blood vessel and monitoring its position on a viewing monitor. Once the stent is properly positioned, the catheter is expanded and the stent separated from the catheter body. The catheter can then be withdrawn from the subject, leaving the stent in place within the blood vessel.

U.S. patent application Ser. No. 240,000 entitled "Radially Expandable Endoprosthesis and the Like" discloses a generally cylindrical stent formed from a wire that is bent into a series of tight bends and then spirally wound about a cylindrical mandrel to form the stent. If a radially outward force is applied to the stent the sharp bends in the wire tend to straighten and the stent diameter enlarges. One technique for implanting this stent uses a deflated balloon catheter to position the stent within a vessel. Once the stent is properly positioned the balloon is inflated to press the stent against the inner wall linings of the vessel. The balloon is then deflated and withdrawn from the vessel, leaving the stent in place.

DISCLOSURE OF THE INVENTION

A stent constructed in accordance with the present invention uses a single elongated wire that is first bent along its length to form a series of tight convolutions. This first fabrication step is similar to the one used in making the stent shown in co-pending application Ser. No. 240,000 mentioned above. This wire is then further formed with the help of a cylindrical mandrel. Instead of spirally winding the wire about the mandrel, a cylindrical form is constructed utilizing a wire interconnection technique which exhibits new and improved expansion characteristics.

The wire is placed over the mandrel in a number of loops which are generally parallel to each other and spaced along the length of the stent by a series of interconnections formed from half hitch junctions. The dimensions of the loops are such that each of such loops has a number of the regularly spaced tight convolutions or bends about its circumference.

The resultant structure has a high degree of flexibility and since each loop forms a generally circular portion of the stent rather than the spiraling portion of the prior art, a more direct and uniform application of expansion forces to the stent occurs.

Use of the invention allows for the omission of one or more stent loops to accommodate branching or crossing vessels within the subject. A backbone is formed by sections which interconnect the half hitch junctions. These sections can either be aligned along the length of the stent or can spiral around the stent's diameter to produce a stent having equal flexibility about the stent circumference.

From the above it is appreciated that one object of the invention is a new and improved stent formed from a series of loops or hoops interconnected to form a cylindrical stent structure. These loops are connected by half hitch junctions that result in more direct and uniform application of expansion forces when the stent is implanted. This and other objects, advantages and features of the invention will become better understood from a detailed description of the preferred embodiment of the invention which is described in conjunction with the accompanying drawings.

BRIEF DESCRIPTION OF THE DRAWINGS

FIG. 1 is a perspective, schematic depiction of a balloon catheter carrying a stent to a delivery portion of a vessel such as a blood vessel;

FIG. 2 is a perspective showing a series of wire loops interconnected with half hitch junctions which combine to create a cylindrical form to define the stent;

FIG. 3 is a perspective view showing a mandrel and a stent fabrication procedure wherein the loops are created about the mandrel as the wire is fed from a sheath which preserves the integrity of tight bends in the wire as the stent is constructed; and FIG. 4 is a schematic depiction on an enlarged scale of a portion of the wire used to fabricate the FIG. 1 stent.

BEST MODE FOR CARRYING OUT THE INVENTION

Figure 2A:
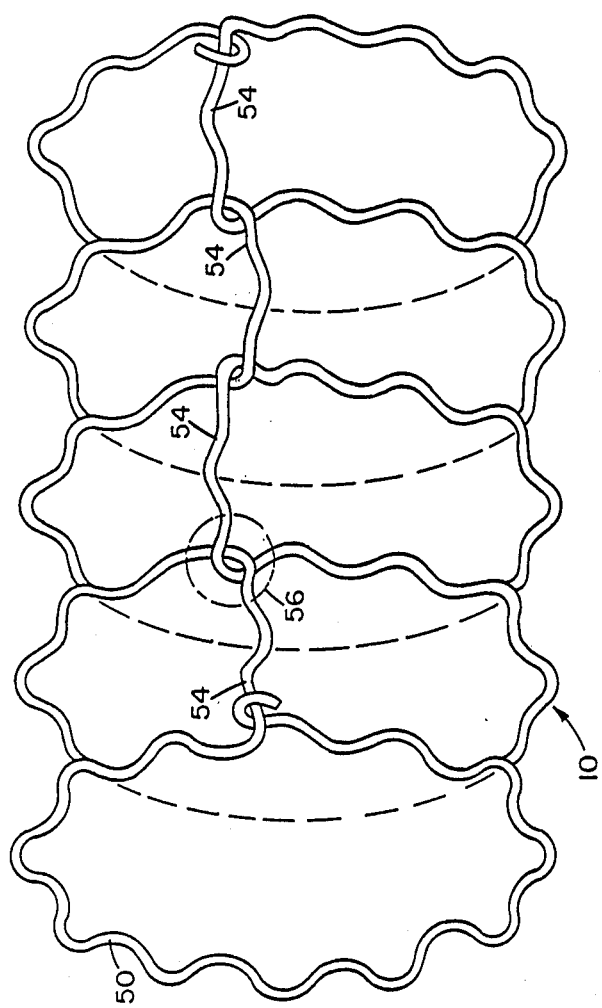
FIG. 2A is an enlarged view of the FIG. 2 stent showing the half hitch junctions in greater detail.

Turning now to the drawings, FIG. 1 shows a cylindrical stent 10 mounted to a balloon catheter 12 which is being routed through a patient's cardiovascular system to a blood vessel region 14. The balloon catheter 12 is of a conventional design and includes a catheter portion that defines a passageway extending from the catheter's proximal to distal end. The passageway allows fluid to be routed to a balloon 16 at the catheter's distal tip to inflate the balloon. As the balloon inflates it exerts a radially outward force against the stent 10 causing the stent to expand into contact with an inner wall of the blood vessel 14.

To release the stent within the blood vessel 14, the balloon 16 is then deflated causing the balloon and stent to separate. The stent 10 is then fixed within the blood vessel due to frictional engagement between the stent and the inner wall lining of the blood vessel 14. The deflated balloon 16 can then be freely withdrawn from the stent. As this procedure is being accomplished, the attending physician can monitor progress of the stent implantation on a viewing monitor to determine the adequacy of the placement.

One feature of the stent 10 constructed in accordance with the present invention is its ability to expand as outward pressure is applied to its length by the balloon 16. This ability stems from a combination of factors discussed in more detail below. One of these factors, however, is the sharp convolutions or bends applied to the wire from which the stent 10 is constructed. These convolutions are applied in a manner described in more detail in pending application Ser. No. 240,000 entitled "Radially Expandable Endoprosthesis and the Like" which is incorporated herein by reference.

Turning now to FIGS. 2 and 2A, the stent 10 includes a series of loops or hoops that are interconnected in the FIG. 2 embodiment of the invention by a backbone 52 running the length of the stent. The backbone 52 is made up of a series of axial or transverse runs 54 that engage each other at half hitch junctions 56 spaced along the stent. Each junction 56 is formed during a fabrication process wherein the wire is looped over itself and extended along the length of the mandrel to form a next subsequent transverse run 54.

The stent 10 of FIGS. 2 and 2A has been depicted in an expanded state where the series of tight bends or convolutions have been partially straightened. The stent is constructed using tantalum wire having a diameter of 5 thousandths of an inch. Before they are straightened by the balloon 16 the bends have typical widths w of 0.048± 0.002 inch and lengths 1 of 0.042± 0.003 inch (FIG. 4).

The fabrication technique for the stent 10 shown in FIGS. 1 and 2 is depicted schematically in FIG. 3. A support mandrel 60 of a generally cylindrical shape is formed to have a diameter of approximately the same diameter as the cylindrical stent 10 in an uncompressed state (0.085 inch ±0.003). The fabrication process begins by forming a first or end most loop 50a about the mandrel 60 and joining the wire at the end of the loop. The wire is then routed along the axial dimension of the mandrel 60 to form a transverse section 54a and then looped around the mandrel 60 to form a second loop 50b. Subsequent to the formation of this second loop 50b, the wire must be routed through a space between the transverse section 54a and the mandrel 60. To facilitate this step without unduly deforming the wire and more particularly the convolutions or bends in the wire, a sheath 70 is fit over the wire to protect the convolutions or bends until the wire is dispensed from the sheath and used to form loops in the stent 10. Thus, when the wire is looped over the mandrel, the end of the wire extending away from the mandrel must be routed underneath the transverse section 54a and then routed along the length of the mandrel 62 to form the half hitch junction 56.

Slipping the wire underneath an existing transverse section (54a for example) forms a half hitch junction. The process of extending the wire along the mandrel 60 to form a run 54 and routing the wire around the mandrel to form a loop 50 continues until the stent 10 of FIG. 2 is completed. Stents of different length and different spacing between loops are contemplated depending upon the specific application for the stent.

The embodiment shown in FIG. 2 has a backbone comprising the plurality of transverse runs 54 in an aligned fashion. It is contemplated, however, that the backbone forming runs could be spaced around the circumference of the stent. It is also contemplated that a second support structure could be added to the stent configuration of FIG. 2 by looping a single convoluted wire around the loops 50 on an opposite side of the stent 10.

One additional feature of the proposed construction is the use of a variable pitch or distance between adjacent loops. This construction would accommodate for example, the use of the stent wherein side or branch vessels are encountered and would allow unimpeded fluid flow to those side or branching vessels through judicious placement of the stent.

While one application of the stent 10 disclosed in the present application is for implantation within a blood vessel. It is appreciated that the stent 10 has applicability for implantation in other vessels within a subject. It is therefore the intent that the invention include all modifications and alterations from the disclosed design falling within the spirit or scope of the appended claims.

I claim:

1. A stent for reinforcing a vessel within a subject comprising a cylindrical support dimensioned to fit within an interior of said vessel constructed from an elongated wire bent to define a series of relatively tightly spaced convolutions or bends, said wire also bent in the form of a plurality of loops spaced along an axial dimension of the stent and connected by a series of half hitch junctions where each of the plurality of loops includes a number of said regularly spaced convolutions around its circumference, said stent being radially expandable from a first outer diameter which fits within said vessel to a second increased diameter which contacts an inner wall surface of said vessel to reinforce said inner wall.

2. The stent of claim 1 wherein the wire is tantalum.

3. The stent of claim 1 wherein an inner diameter of the stent is dimensioned to frictionally engage a non-inflated balloon catheter and be carried by the non-inflated balloon catheter into a blood vessel.

4. The stent of claim 1 wherein the plurality of loops are regularly spaced along the length of the stent and are interconnected by lengths of convoluted wire that are aligned along the length of the stent to form a relatively straight backbone to said stent.

5. The stent of claim 4 wherein gaps are left along the length of the stent to accommodate branches in the vessel so that the stent does not block off fluid flow through the branch.

6. The stent of claim 1 wherein the plurality of loops are regularly spaced along the length of the stent and are interconnected by lengths of convoluted wire that are offset around the diameter of the stent to define a backbone having a relatively wide pitch that spirals about the stent.

7. A method of fabricating a generally cylindrical stent for insertion into a body vessel comprising the steps of:
   (a) bending an elongated wire in a series of relatively tight convolutions or bends;
   (b) providing a cylindrical mandrel of a dimension smaller than an inner diameter of the vessel into which the stent is to be inserted;
   (c) wrapping the elongated wire around the mandrel to form a series of loop segments and interconnecting said loop segments by half hitch junctions and wire portions that connect successive loop segments along an axial dimension of the cylindrical mandrel; and
   (d) removing the elongated wire from the mandrel to define a throughpassage for fluid passage through the stent in a region occupied by the cylindrical mandrel.

8. The method of claim 7 wherein the series of loops are connected by a sequence of wire portions that are radially spaced around the circumference of the stent.

9. The method of claim 7 wherein the series of loops are connected by a sequence of wire portions that align along the length of the stent to form a relatively straight backbone to the stent.

10. The method of claim 7 wherein subsequent to the removal of the stent from the mandrel one or more loops are removed from the stent to accommodate branching vessels and allow unimpeded fluid flow to said branching vessels after the stent is positioned within the vessel.

* * * * *